(12) United States Patent
Perten

(10) Patent No.: US 6,250,147 B1
(45) Date of Patent: Jun. 26, 2001

(54) DEVICE AND METHOD FOR ANALYZING STARCH-CONTAINING PRODUCT

(75) Inventor: Jan Perten, Djursholm (SE)

(73) Assignee: Larena AG, Cham (SE)

( * ) Notice: Subject to any disclaimer, the term of this patent is extended or adjusted under 35 U.S.C. 154(b) by 0 days.

(21) Appl. No.: 09/254,480

(22) PCT Filed: Jul. 8, 1998

(86) PCT No.: PCT/SE98/01350

§ 371 Date: Mar. 8, 1999

§ 102(e) Date: Mar. 8, 1999

(87) PCT Pub. No.: WO99/02965

PCT Pub. Date: Jan. 21, 1999

(30) Foreign Application Priority Data

Jul. 8, 1997 (SE) .................................................. 9702639

(51) Int. Cl.$^7$ ............................. G01N 7/20; G01N 11/10; A23L 1/05
(52) U.S. Cl. ............................. 73/169; 73/54.25; 426/578
(58) Field of Search .................................. 73/169, 54.25, 73/54.26, 54.31, 54.24, 54.36, 54.23, 54.14, 54.41; 521/84.1; 426/619, 457, 578, 549

(56) References Cited

U.S. PATENT DOCUMENTS

| | | | |
|---|---|---|---|
| 3,673,125 | * | 6/1972 | Takahashi et al. .................. 521/84.1 |
| 3,714,814 | * | 2/1973 | Schneiders et al. ................. 73/54.25 |
| 3,792,956 | * | 2/1974 | Hyldon ................................ 426/619 |
| 3,917,866 | * | 11/1975 | Purves et al. ........................ 426/457 |
| 4,159,982 | * | 7/1979 | Hermansson ......................... 530/360 |
| 4,215,152 | * | 7/1980 | O'Rourke ............................. 426/579 |
| 4,303,452 | * | 12/1981 | Ohira et al. ............................ 127/32 |
| 4,428,967 | * | 1/1984 | Goering et al. ......................... 426/28 |
| 4,435,429 | * | 3/1984 | Burrows et al. ........................ 426/18 |
| 4,752,449 | * | 6/1988 | Jackson et al. ......................... 422/73 |
| 4,774,328 | * | 9/1988 | Friedman et al. ..................... 536/102 |
| 4,789,557 | * | 12/1988 | Friedman et al. ..................... 426/578 |
| 4,799,378 | * | 1/1989 | Portman, Jr. et al. ............... 73/54.27 |
| 4,811,593 | * | 3/1989 | Miura et al. .......................... 73/54.26 |
| 4,879,897 | * | 11/1989 | Booth et al. .......................... 73/54.31 |
| 4,905,499 | * | 3/1990 | Miura et al. ........................... 73/32 A |
| 4,981,710 | * | 1/1991 | McComber et al. .................. 426/578 |
| 5,120,562 | * | 6/1992 | Furcsik et al. ........................ 426/549 |
| 5,164,215 | * | 11/1992 | Furcsik et al. ........................ 426/549 |
| 5,389,388 | * | 2/1995 | Gusek .................................. 426/242 |
| 5,571,952 | * | 11/1996 | Kauzlarich ........................... 73/54.24 |
| 5,604,302 | | 2/1997 | Wang . |

FOREIGN PATENT DOCUMENTS

| | | |
|---|---|---|
| 195 02 682 | 9/1995 | (DE) . |
| 44 37 126 | 4/1996 | (DE) . |
| 0 428 241 | 5/1991 | (EP) . |
| WO 87/01198 | 2/1987 | (WO) . |
| WO 95/10042 | 4/1995 | (WO) . |

\* cited by examiner

Primary Examiner—Hezron Williams
Assistant Examiner—Jay L. Politzer
(74) Attorney, Agent, or Firm—Young & Thompson

(57) ABSTRACT

A suspension of a starch-containing product in heated during agitation, whereby the viscosity is registered as a function of the temperature. A curve over the relationship between viscosity an temperature is treated as a property profile for the sample and is compared with another known curve in order to determine the heating properties for the sample. A device for this analysis has an agitator (7), the drive means (10, 11) of which has a power sensor (12) for sensing the power which the agitator is subjected to during the agitating, whereby a measure of the viscosity is obtained. A temperature sensor (13) senses the temperature of the sample.

14 Claims, 3 Drawing Sheets

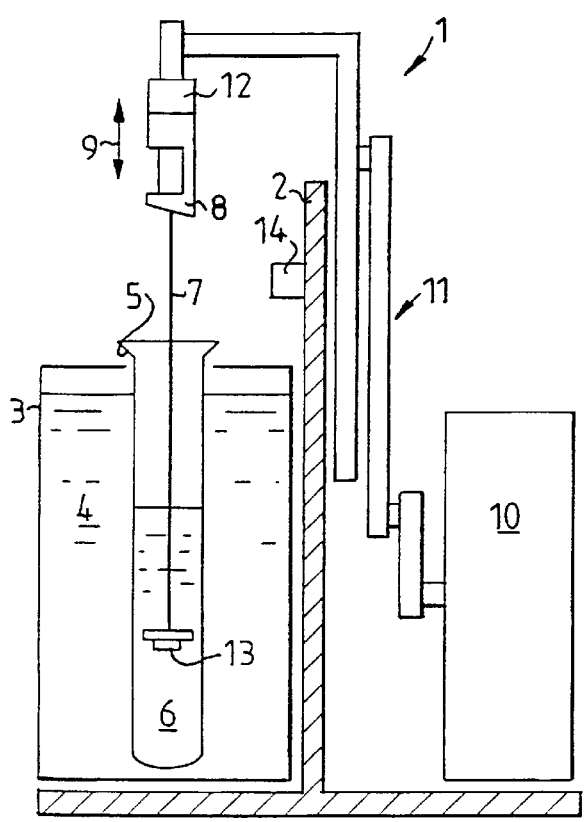
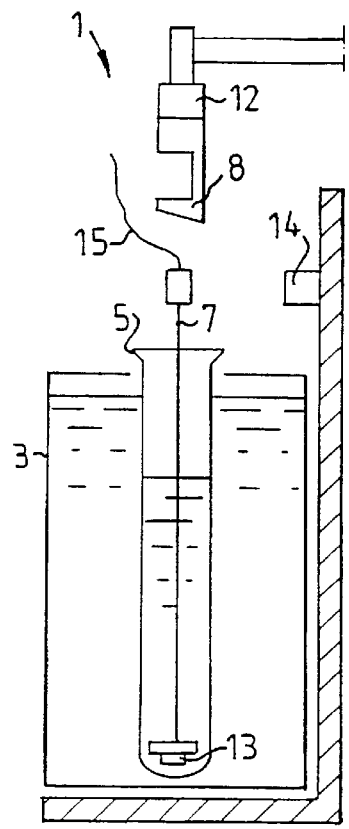
FIG.1
FIG.2
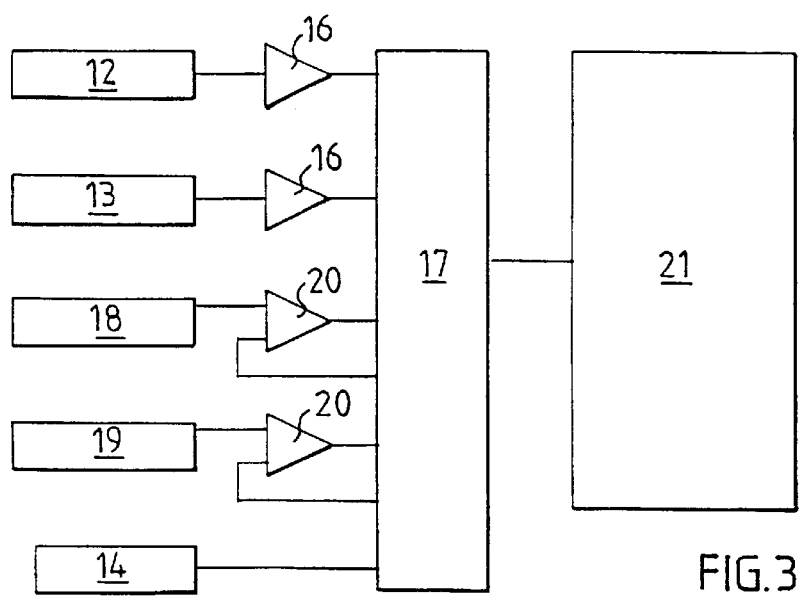
FIG.3

DEVICE AND METHOD FOR ANALYZING STARCH-CONTAINING PRODUCT

FIELD OF THE INVENTION

The invention relates to a method of analyzing an example of a starch-containing product. The invention also relates to a device for such analyses.

STATE OF THE ART

It is well known that starch with the addition of fluid, often water, thickens during heating and then thins out with continued heating as a consequence of that the enzyme alpha-amylas converts the starch. Depending on the amount and strength of this enzyme and the resistance of the starch to the enzyme, various degrees of conversion of the starch or alpha-amylas activity are obtained under predetermined conditions.

A well-established, quick and reliable method for the determination of alpha-amylas activity has for many years been the drop number method. In accordance with this method a special apparatus is used, where a precision test tube containing a suspension of a precise sample amount of the actual starch-containing product in a precise amount of distilled water is placed in a boiling waterbath, whereafter agitating of the sample takes place for a certain time with a special agitator, which after finished agitating is allowed to drop, and the time it takes for the agitator to fall a precise distance is measured. The total time in seconds, from that the test tube has been placed in the waterbath and until the agitator after finished agitating has fallen a predetermined distance, defines a drop number value, which consequently forms a measure of the degree of alpha-amylas activity in the actual sample. The drop number value consequently varies according to the properties of the sample.

For e.g. wheat samples the drop number value can vary between approx. 62, which indicates a high degree of alpha-amylas activity, and approx. 400, which indicates a low alpha-amylas activity. For rye samples the drop number interval is less, approx. 62 to approx. 200, with the same proportions between the amount of samples and the amount of water.

During the baking of bread from wheat resp. rye it has been shown that certain drop number values are instructive for predicting the baking result in connection with the processes which are usually used in the western world for baking. For wheat, a drop number of approx. 250 is considered to define a flour which gives a good baked product. Lower drop numbers tend to give a sticky bread crumb while higher drop numbers, e.g. over 400, gives a dry crumb and also a smaller bread volume.

The drop number method is today an established standard method for the branch organizations around the world for the determination of alpha-amylas activity. Generally for this method, the drop number apparatus, which is manufactured by the company Perten Instruments AB, Huddinge, Sweden, is used The usability of the drop number method is amongst other things dependent on the fact that the temperature profile during testing has been shown to have a large correspondence with the temperature profile in bread during bakaring, at least in the critical region of 60°–90° C. Experience has, however, shown that the drop number does not give exhaustive information on the properties of a raw material, but two raw materials with the same drop number can have different properties in varying respects.

It is also previously known to use different methods for determining how the viscosity of a water suspension of a sample changes when the suspension is heated up and then allowed to cool. In such a standard method according to Brabender (Amylograph) the suspension is heated up from 25° C. to 95° C. with an even rate of temperature increase and with constant agitating. When the temperature of 95° C. is obtained, the temperature is held at this value for 30 minutes (first holding period) with continued agitating. Thereafter the suspension is cooled to 50° C. at a certain rate and then held at this temperature for 30 minutes (second holding period). The agitation resistance, i.e. the torque, herewith gives a measure of the viscosity. Here one has, however, been especially interested in certain places on a curve which gives viscosity as a function of time. First and foremost, one has looked at the initially obtained peak value of the viscosity, but also the viscosity value when reaching 95° C. has been of interest Then one has been interested in the viscosity value at the end of the first holding period, when the temperature is still 95° C. Another viscosity value of interest has been the point where the temperature has dropped to 50° C., and finally at the end of the second holding period, i.e. after 30 minutes at 50° C. This method is time-demanding and is aimed at giving the viscosity values at special stages of the testing at special temperatures.

In the modem food industry the requirement is growing for, in a simple and reliable way, to be able to determine the properties of a raw material so that e.g. it becomes easy to select the right raw material for a certain product which can be made according to a special process, in order to obtain an even and good quality for the product. There is a corresponding requirement for being able to sort different raw materials for suitable processes.

The named methods have deficiencies in this respect, wherefore it is desirable with simple means to be able to bring forth better methods for determining the properties, especially with respect to the starch and enzyme properties, of different starch-containing products.

OBJECT OF THE INVENTION

The object of the invention is to make it possible to simply obtain refined and clear information about the properties of the starch and the influence of the alpha-amylas enzyme in the starch in a temperature region which is important for the starch. The object is also to produce a reliable device which makes it possible to perform the desired analysis.

DESCRIPTION OF THE INVENTION

A proposed method in accordance with the invention to perform the analysis is stated below. Advantageous variants of this method are also disclosed. By studying the changes of the viscosity of the sample during heating, a property profile is obtained for the sample with respect to its heating properties and by comparing this property profile with at least on corresponding predetermined property profile, it is possible to more closely determine the nature of these properties. It has been shown to be especially rewarding to study the viscosity changes as a function of the temperature in the sample. In this way a picture is obtained of how the sample behaves in a manufacturing process.

In accordance with the invention it has been shown that an excellent device for analysis is obtained through modifying a known falling numbers apparatus. This solution furthermore offers the extremely large advantage that the apparatus obtained can still be used for falling number determination, wherein a more complete analysis of a sample can be made than that which was previously possible.

DESCRIPTION OF THE FIGURES

The invention is explained in more detail in the following with the help of the accompanying drawings, which show examples of embodiments, where:

FIG. 1 shows schematically a device for analyzing during agitating, made in accordance with the invention, FIG. 2 shows the device in FIG. 1 but when the agitator has been allowed to fall a certain distance, FIG. 3 shows the construction principle of the control system of the device in FIGS. 1 and 2, and FIGS. 4–9 show viscosity changes as a function of the temperature in the sample for a number of different starch-containing raw materials.

DESCRIPTION OF PREFERRED EMBODIMENTS

Figure 4:
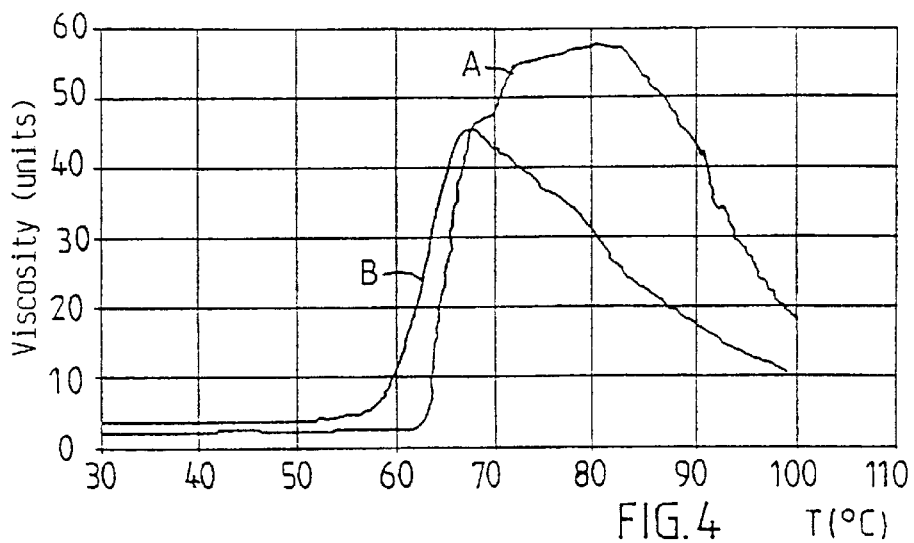

FIG. 1 shows an analysis device 1 according to the invention, where a falling number apparatus of conventional type is modified in order to permit viscosity measuring and temperature measuring in a water suspension of a starch-containing product during analysis. Falling number apparatuses of different models have been marketed for many years by Perten Instruments AB in Huddinge, Sweden, and are well known to the person skilled in the art. The construction of the equipment will therefore only be described to the extent which is necessary in order to understand the invention.

On a stand 2 there is a container 3 with a temperature-regulated waterbath 4 in which a test tube 5 is lowered. The test tube 5 contains a water suspension 6 of a starch-containing product which is to be analyzed. Lowered into the test tube 5 and the water suspension 6 is an agitator 7, the upper end of which rests in a holder 8 with the help of which the agitator 7 can be moved up and down in the test tube in the direction of the double arrow 9. On the stand 2 there is also a motor 10, which via a mechanism 11 and a power sensor 12 can set the holder 8 in movement up and down at a speed which can vary through changing the rotational speed of the motor. In the lower end of the agitator 7 there is a temperature sensor 13 for sensing the actual temperature in the contents of the test tube 5.

FIG. 2 shows how the agitator 7 after finishing agitating has been released by the holder 8 and falls into the test tube 5. A position sensor 14 indicates when the agitator 7 has reached an intended lower position. A conductor 15 passing through the agitator 7 connects the temperature sensor 13 with a measuring unit.

From FIG. 3 is evident how the control system for the analysis device 1 in FIGS. 1 and 2 is constructed. The power sensor 12 and the temperature sensor 13 are each via their own measurement amplifier 16 connected to a control unit 17 where signal processing occurs. The position sensor 14 is directly connected to this control unit 17. A revolution sensor 18 for the motor 10 and a temperature sensor 19 for the waterbath 4 are each connected via their own control amplifier 20 to the control unit 17, which in turn is connected to a computer 21 for checking and the presentation of falling numbers and alternative curves for e.g. power/time, temperature/time and power/temperature.

The power sensor 12 can advantageously be a strain gauge sensor or some other type of sensor, e.g. of optical or piezoelectrical type, which is placed at a suit-able place on the holder 8 in order to measure its deformation during agitating. This deformation, can through calibration, be made to represent a certain resistance to motion or viscosity in the contents of the test tube. With the help of the control unit 17 it is possible to change the rotational speed of the motor 10, and in this way the up and down movements per time unit which the agitator 7 can perform. It is also possible with the help of the control unit 17 to control the temperature in the water-bath 4 to different temperatures in the region 60° C.–100° C. in order to obtain different measuring conditions. Normally, however, the temperature in the waterbath is held at 100° C.

Testing in accordance with the invention normally takes place in the following way. A precise, ground amount of the raw material which is to be tested is mixed through shaking with a precise amount of distilled water in the test tube 5, which thereafter is placed in the holder 3 and its waterbath 4, the temperature of which is 100° C. After five seconds the agitating begins automatically and continues while the contents of the test tube heat up. During the heating up, the viscosity changes are registered as a function of the temperature in the sample. A number of such results are shown in FIGS. 4–9, where the viscosity is given in units related to the equipment used.

FIG. 4 shows a comparison between two different sorts of flour, where curve A represents the first type of flour and the curve B the second type of flour. In both cases the mixing relationship was 7 g/25 ml, i.e. 7 g of flour were mixed with 25 ml of distilled water. The temperature of the waterbath 4 was 100° C., and the stroke frequency for the agitator 7 was 2 Hz.

The flour A has a viscosity maximum of 57.3 units at the temperature 80.1° C., while the corresponding value for the flour B is 45.5 units at 67.5° C. The viscosity quotient between the flours A and B is consequently 57.3/45.5=1.26, and the difference in temperature between the two viscosity maxima of the two curves, which have completely different profiles, is 12.6° C.

Conventional flour data for the flours A and B is the following:

|  | Flour A | Flour B |
| --- | --- | --- |
| Viscosity maximum based on Amylogram | 1050 AE at 89.3° C. | 215 AE at 68.9° C. |
| Drop number | 360 | 179 |
| Ash content, % | 0.56 | 1.12 |
| Protein content, % | 13.2 | 12.4 |
| Water content, % | 15.0 | 13.0 |
| Gluten, % | 28.3 | — |
| Gluten index | 84 | — |

As is evident according to the invention a considerably larger correspondence between the maximum viscosity levels is obtained than with conventional methodology.

Figure 5:
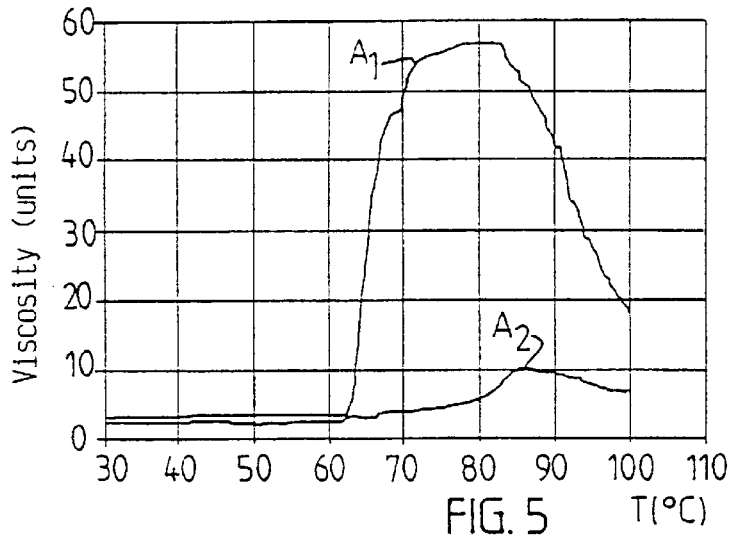

FIG. 5 shows tests with the flour A in two different mixing relationships. For the upper curve A the mixing relationship is 7 g/25 ml, i.e. the same as in FIG. 4, while for the lower curve $A_2$ the mixing relationship is only half as big, i.e. 3.5 g/25 ml. As is evident, for the lower mixing relationship considerably lower viscosity values are obtained. The curve $A_1$ gives a viscosity maximum of 57.3 units at 80.1° C. while the corresponding value for the curve $A_2$ is 10.2 units at 86.4° C. The viscosity maximum consequently drops and is shifted towards a higher temperature at lower mixing relationships. The curves $A_1$ and $A_2$ have substantially different profiles.

The waterbath temperature and the agitating frequency were the same as in FIG. 4.

Figure 6:
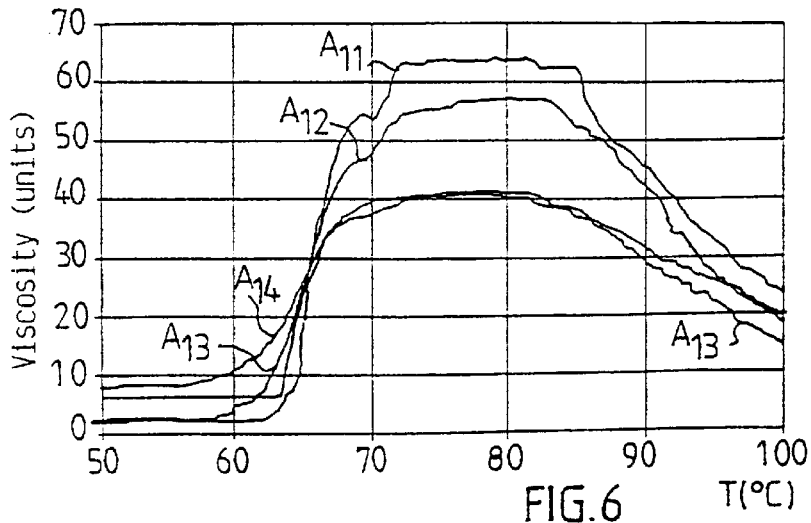

FIG. 6 shows, for the flour A, how the viscosity varies as a function of temperature at different stroke frequencies for the agitator at a waterbath temperature of 100° C. and a mixing relationship of 7 g/25 ml.

The curves $A_{11}$, $A_{12}$, $A_{13}$ and $A_{14}$ each represent a stroke frequency of 2.85, 2.0, 1.25 and 1.0 Hz for the agitator. The curve $A_{11}$ has a viscosity maximum of 58.1 units at 80.1° C. Corresponding values are for $A_{12}$ 55.1 units at 78.6° C., for $A_{13}$ 38.8 units at 79.0° C., and for $A_{14}$ 32.6 units at 77.7° C. The viscosity maximum is consequently shifted towards a lower value and a lower temperature with increasing agitator frequency.

Figure 7:
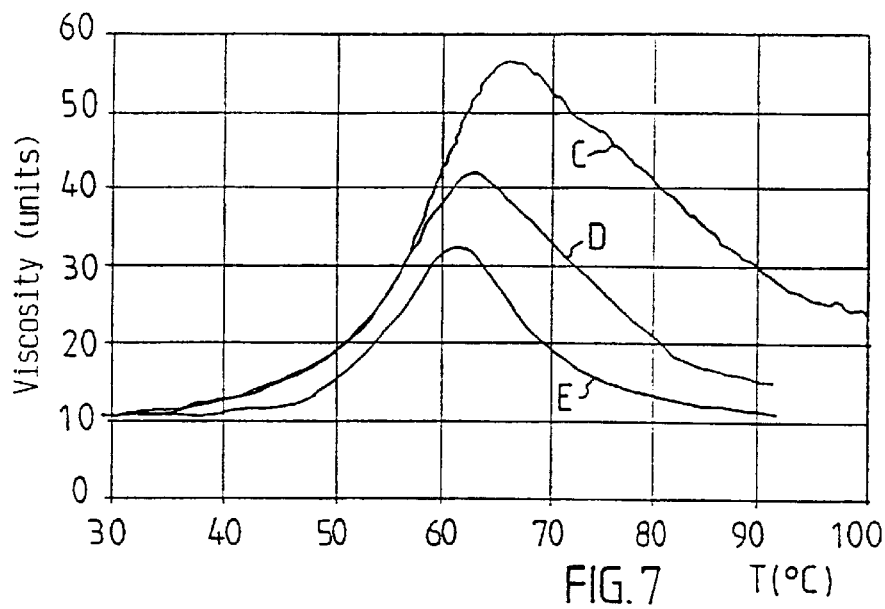

FIG. 7 shows tests with three different flours C, D and E from Germany, according to corresponding curves. The curve C gives a viscosity maximum of 56.8 units at 65.9° C. while the corresponding values for curve D are 42.1 units at 62.7° C. and for curve E 32.4 units at 61.3° C.

Conventional flour data for the flours C, D and E are the following:

|  | Flour C | Flour D | Flour E |
| --- | --- | --- | --- |
| Viscosity maximum based on Amylogram | 675 AE at 69.5° C. | 375 AE at 63.0° C. | 185 AE at 60.0° C. |
| Drop number | 254 | 127 | 62 |
| Water content, % | 13.3 | 12.8 | 12.4 |

The mixing relationship was 6.8 g/25 ml for all of them. Temperature of the waterbath 100° C. and the agitator frequency 2 Hz.

According to conventional flour data, as is evident, halving the drop number leads to approximately halving of the viscosity maximum. According to tests performed now, however, the quotient between the viscosity maxima is the following: C/D =1.35 and D/E=1.30. The three different flour types consequently each gave their own special curve profile which indicates different properties.

Figure 8:
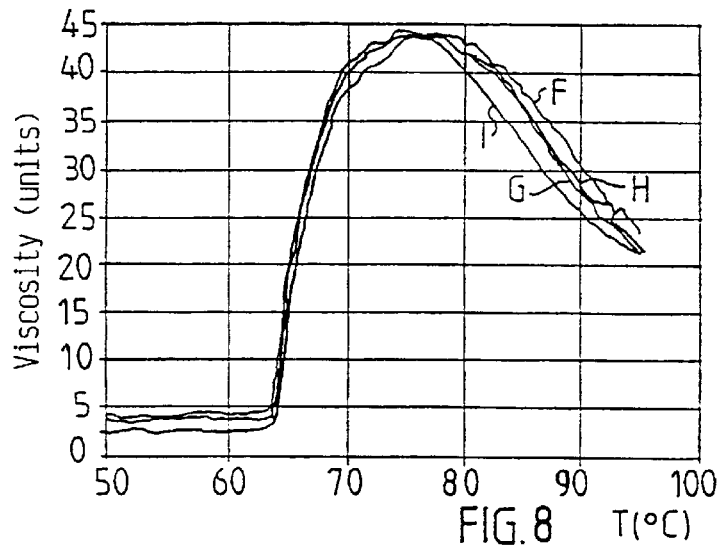

FIG. 8 shows tests with four different Swedish flours F, G, H and I with falling numbers in the interval 230–292. As is evident, the curves F, G, H and I lie extremely close to each other and are difficult to separate. The viscosity maximum lies for all of them at approximately 44 units at a temperature of approx. 76° C. In all tests thickening begins at approx. 65° C. The test conditions are the same as in FIG. 6.

Figure 9:
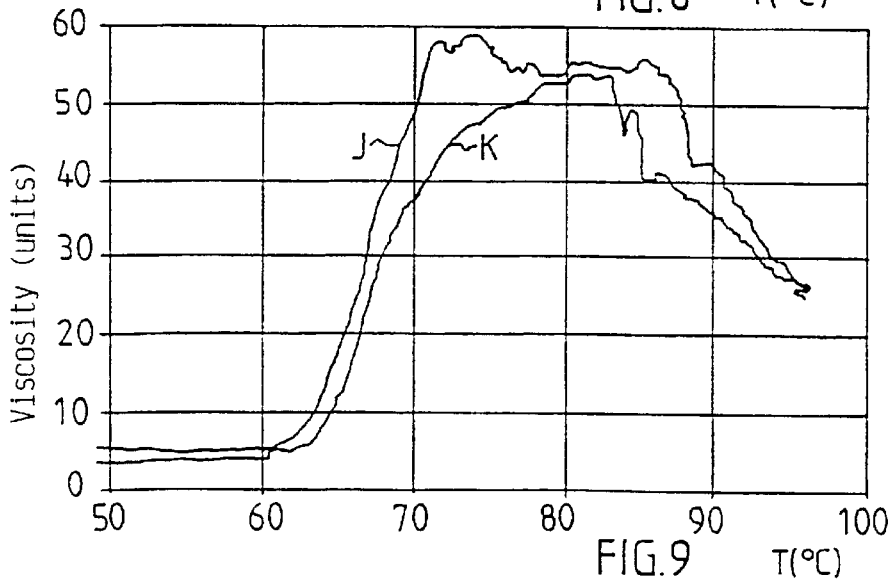

FIG. 9 shows tests with an Austalian flour according to curve J and a Spanish flour according to curve K. Curve J gives a viscosity maximum of 58.7 units at 73.2° C. and the corresponding value for curve K is 55.5 units at 85.0° C. The same test conditions as in FIGS. 7 and 8. The flour J had a falling number of 700 and a water content of 11.7%. The corresponding values for the flour K were 540 and 12.2%.

Despite the large difference in drop number for the two flours, according to the curves in FIG. 9, similar maximum levels for the viscosity were achieved for the two flours but at clearly different temperatures.

As is evident above, in the different tests, result curves are obtained where not only the position for the maximum viscosity varies but also the general profile of the curves has different appearances. A comparison between e.g. FIGS. 4 and 7 shows that the viscosity change in the beginning is more abrupt in FIG. 4 than in FIG. 7 and subsequently is considerably steeper and more constant than in FIG. 7. Curve A has a rather wide peak while the other curves have a narrow peak, and drop more slowly after the maximum than curve A. It is on the basis hereof obvious that the starch in the different samples behaves differently, i.e. the raw materials in the different samples have different properties. This means that a certain curve profile indicates certain properties while another curve profile indicates other properties. This consequently makes it possible to distinguish different raw materials with respect to starch properties, either in certain sections along the curve or with respect to the whole curve. In order to more closely be able to determine the meaning of a certain curve, it is suitable to perform a comparison with a corresponding curve for a predetermined sample.

On the basis of a so obtained analysis of the starch properties of the raw material, it is possible to determine the best method of using the raw material in question, i.e. each raw material can more easily be used in the best way.

Through the selected testing method a uniform and reproducible heat transfer to the sample from the surrounding waterbath is obtained. A large advantage is also that conventional falling number measuring can take place with the same conditions concerning temperature change and agitator frequency. This increases the reliability of the analysis, as several properties can be related to each other.

A consequence of the uniform heat transfer is also that the temperature increase takes place at an even rate, and therefore the temperature scale on the basis hereof in principle can be replaced by a time scale, after suitable calibration. Instead of measuring temperature with a temperature sensor it is consequently possible, on the basis of a calculation algorithm and suitable base parameters, to obtain a temperature value.

In a comparison between different test curves the curve slope at different positions is of great interest. It can, for example, be suitable to characterize a product through stating an average slope, before or after maximum, between two points, e.g. points representing 25% and 75% of the viscosity maximum, or other suitable values. It can also be of interest, for example, to define the width of the maximum viscosity as a temperature interval between two points on the curve representing e.g. 85% of the maximum viscosity. As is evident, a large number of definitions can be selected, depending on requirements and desires.

In manufacturing processes where heating takes place, e.g. in baking, it is of great interest to know how the properties of the starch change during heating and thereby can influence the intended result. By performing an analysis according to the invention, it will be possible, more reliably than previously, to be able to select the right raw material for a certain process and vice versa, as knowledge of the raw material and the process can be improved.

What is claimed is:

1. Method of analyzing a sample of a starch-containing product, comprising the steps of:

mixing a sample with fluid to form a suspension;

heating and agitating the sample;

registering the suspension viscosity as a function of a predetermined parameter and presenting as a curve;

considering the obtained viscosity variation curve as a property profile for the sample;

comparing at least a section of this property profile to a corresponding section of at least one corresponding, predetermined property profile for a reference sample similarly obtained; and on the basis of this comparison, determining properties of the sample.

2. Method according to claim 1, characterized in that the temperature in the suspension is used as a predetermined parameter.

3. Method according to claim 1, characterized in that heating takes place through a container with the sample being placed in water with a chosen temperature, preferably boiling water.

4. Method according to claim 2, characterized in that the slope of the curve at least at one predetermined point before the peak of the curve representing the maximum viscosity, is used as a measure of the thickening properties of the sample.

5. Method according to claim 2, characterized in that the slope of the curve at least at one predetermined point after the peak of the curve representing the maximum viscosity, is used as a measure of the thinning properties of the sample.

6. Method according to any of claim 1, characterized in that time is used as a predetermined parameter.

7. Method according to claim 1, characterized in that agitating takes place by an agitator moving up and down essentially in the vertical direction, and that the same agitator is also released for determining a falling number value of the sample.

8. Device for analysis of a sample of a starch-containing product, comprising:

heating device intended for a sample container, an agitator intended for placement in the sample container; and a drive means belonging to the agitator and which is arranged to bring the agitator into movement up and down in the vertical direction, the drive means being provided with a power sensor for sensing the power which the agitator is subjected to during its movement in the sample in the sample container, means for, as a function of a predetermined parameter, registering this power as a measure of viscosity of the sample, and a holder, which is arranged to be able to release the agitator during the use of the device for a falling number determination.

9. Device according to claim 8, further comprising a sensor (13) for sensing the temperature of the sample.

10. Device according to claim 9, wherein the sensor is a temperature sensor (13) which is arranged in the agitator (7).

11. Device according to claim 8, wherein the power sensor (12) comprises a strain gauge.

12. A method of analyzing a sample containing starch, the method comprising the steps of:

heating the sample;

moving an agitator up and down in a vertical direction within the sample;

determining the viscosity of the sample by measuring the power to which the agitator is subjected during the up and down movement; and releasing the agitator to determine a falling member.

13. The method of claim 12, comprising the further step of developing a viscosity vs. temperature viscosity variation curve as a property profile for the sample.

14. The method of claim 13, comprising the further step of comparing the developed sample viscosity variation curve to a reference curve to determine heating properties of the sample.

* * * * *